(12) United States Patent
Xu et al.

(10) Patent No.: US 9,833,539 B2
(45) Date of Patent: Dec. 5, 2017

(54) E-POLYLYSINE HYDROGEL AND PREPARATION METHOD AND APPLICATION THEREOF

(71) Applicant: NANJING TECH UNIVERSITY (CN), Nanjing (CN)

(72) Inventors: Hong Xu, Nanjing (CN); Bo Chi, Nanjing (CN); Rui Wang, Nanjing (CN); Xiaohai Feng, Nanjing (CN); Sha Li, Nanjing (CN); Jinfeng Liang, Nanjing (CN); Pingkai Ouyang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 38 days.

(21) Appl. No.: 15/100,222

(22) PCT Filed: Dec. 28, 2013

(86) PCT No.: PCT/CN2013/090814
§ 371 (c)(1),
(2) Date: May 27, 2016

(87) PCT Pub. No.: WO2015/096170
PCT Pub. Date: Jul. 2, 2015

(65) Prior Publication Data
US 2017/0000924 A1  Jan. 5, 2017

(30) Foreign Application Priority Data

Dec. 25, 2013 (CN) .......................... 2013 1 0728964

(51) Int. Cl.
  C08G 69/40 (2006.01)
  A61L 26/00 (2006.01)
  C08J 3/075 (2006.01)
  A61L 15/32 (2006.01)
  A61L 15/60 (2006.01)
  C08G 69/10 (2006.01)
  C08G 69/48 (2006.01)
  C12P 13/08 (2006.01)

(52) U.S. Cl.
  CPC .......... *A61L 26/0019* (2013.01); *A61L 15/32* (2013.01); *A61L 15/60* (2013.01); *A61L 26/008* (2013.01); *A61L 26/009* (2013.01); *A61L 26/0047* (2013.01); *C08G 69/10* (2013.01); *C08G 69/40* (2013.01); *C08G 69/48* (2013.01); *C08J 3/075* (2013.01); *C12P 13/08* (2013.01); *A61L 2300/252* (2013.01); *A61L 2300/802* (2013.01); *A61L 2430/34* (2013.01); *C08J 2377/04* (2013.01); *C08J 2389/00* (2013.01)

(58) Field of Classification Search
  CPC ................. C08G 69/40; C08G 69/08
  See application file for complete search history.

(56) References Cited

U.S. PATENT DOCUMENTS

2014/0163133 A1* 6/2014 Chan .................. A61L 27/227
                                                   523/105

* cited by examiner

*Primary Examiner* — Michael Pepitone
(74) *Attorney, Agent, or Firm* — CBM Patent Consulting, LLC (57) ABSTRACT

The present invention discloses a ε-polylysine hydrogel and the preparation method and application of the as-described ε-polylysine hydrogel. The polylysine hydrogel is non-toxic to a recipient, and has biodegradability and biocompatibility. The wound tissue healing material prepared by the present invention can be used in wound tissue adhesion in an efficient, stable, safe manner.

18 Claims, 4 Drawing Sheets

ε-POLYLYSINE HYDROGEL AND PREPARATION METHOD AND APPLICATION THEREOF

This application is the U.S. national phase of International Application No. PCT/CN2013/090814 Filed on 28 Dec. 2013 which designated the U.S. and claims priority to Chinese Application Nos. CN 201310728964.3 filed on 25 Dec. 2013, the entire contents of each of which are hereby incorporated by reference.

TECHNICAL FIELD

The present invention relates a ε-polylysine hydrogel and its preparation method and application, and belongs to medical technology application field.

BACKGROUND OF THE INVENTION

Hydrogel medical wound dressing is a novel developed wound dressing in recent years. Compared to the traditional dressing, the hydrogel can promote better healing of the wound, and relieve pain of patient. It can improve microenvironment of the wound surface, and inhibit growth of bacteria. The hydrogel is especially suitable for use in common trauma of body surface, such as abrasion, scratching, bedsore and other skin injuries. For these wounds, traditionally, the doctor generally treats them with sterile gauze and topical antibiotics. However, the gauze is prone to adhere to skin wound tissue, at time of dressing change it often destroys new epithelial and granulation tissues, causing hemorrhage, this is unbeneficial to wound healing and makes the patient painful. When the hydrogel dressing is applied onto the wound, it will not adhere to the wound, not destroying new tissue, furthermore it can kill various bacteria, avoiding wound infection. The hydrogel dressing is a kind of good wound surface dressing, it is a polymeric swelling body containing certain moisture with a three-dimensional network structure, and it has good water absorption and biocompatibility, it can closely fit with an uneven wound surface without adhesion, and reduce bacterial growth and easy to be replaced, and it can be permeated with various drug components and growth factors, promoting wound healing. The hydrogel perse has a large heat capacity, it has a mild cooling effect to the wound, and it can relieve pain of the wound. Therefore, scholars at home and abroad have made extensive research on the hydrogel dressing and obtained some achievements. At present, the hydrogel dressing occupies most part of the global dressing and bandage market.

Currently, the fibrin glue, cyanoacrylate, chitosan etc have been commercially used in wound dressing, but they respectively have shortcomings thus restricting their wide application in clinical surgery. For example, the fibrin glue is primarily derived from animal blood tissue, thus there exists a risk of blood virus infection; for cyanoacrylate, although it has a good hemostasis effect but due to its high cytotoxicity it is not best choice for wound tissue healing; for chitosan, it has a rapid hemostasis function, and can be made intovarious medical dressing products, but its poor mechanical property, high brittleness, low water-solubility have become major obstacles to its application in surgical wound dressing.

ε-polylysine is a kind of natural polymeric material forming hydrogel, it is obtained by microbial fermentation. The molecular weight of ε-polylysine is between 3 kDa and 5 kDa, being similar to the protein composition and function of nature extracellular matrix ECM), and it has significant advantage over other wound dressing material, which is in the following aspects: first, there are a large number of amino active groups on molecular chain, it binds with hydrogen ion to be positively charged and form a cationic polymer in aqueous solution or acidic environment, such cationic polymer can binds to cell surface in order to achieve trauma tissue adhesion; second, as polylysine is a natural polymeric material, having good biocompatibility, and its degradation product lysine is an essential amino acid for human, finally, polylysine is an amino acid polymer, it has good water-solubility, overcoming the issue of being difficult dissolved in water of many tissue healing materials, but polylysine has a large number of active amino groups, it binds with hydrogen ion in water solution or acidic environment to be positively charged and destroys tissue cell structure to a certain degree, and it has certain cytotoxicity, in order to make it safely used in wound tissue adhesion, it must be modified to reduce cytotoxicity.

PEG is a kind of polymer with a good water-solubility and biocompatibility, it is widely used in surface modification of biomaterial, and modification protection of polypeptide and protein drug. PEG modification has an obvious inhibitory effect to some induced apoptosis, significantly reduce content of intracellular ROS (reactive oxygen species), and make mitochondrial membrane potential ri be stable. PEG modification reduces the cytotoxicity of polylysine mainly by reducing production of intracellular ROS (reactive oxygen species), high modification degree has an obvious effect of reducing toxicity. PEG modified polylysine can significantly reduce cytotoxicity of polylysine, and the ability of reducing toxicity are obviously enhanced with increase in molecular weight and modification degree of PEG.

The hydrogel medical material currently used in wound dressing are primarily divided into chemically synthesized and biopolymer material, but there are many shortcomings such as low mechanical strength, poor biocompatibility, and high cytotoxicity during formation of hydrogel material.

SUMMARY OF THE INVENTION

A technical problem to be resolved by the present invention is to provide a medical wound dressing polylysine hydrogel.

Another technical problem to be resolved by the present invention is to provide a preparation method of the above-described hydrogel.

A final technical problem to be resolved by the present invention is to provide applications of the above-described hydrogel.

To resolve the above-described technical problems, the technical solution adopted by the present invention is as follows:

A ε-polylysine hydrogel, it has the following constitutional unit:

wherein, n is any natural number of 20 to 30, m is any natural number of 50 to 70.

A preparation method of the as-described ε-polylysine hydrogel, it includes the following steps:

(1) Polyethylene glycol (PEG) is dissolved in dichlormethane. Then 4-dimethylaminopyridine (DMAP) and triethylamine (TEA) are added into the PEG solution at room temperature and reacted for 20~150 minutes. Afterwards, the reaction solution is added dropwisely to a solution of p-nitrophenylchloroformate (PNC) in dichlormethane under room temperature and inert gas shrouding condition and reacted for 12~72 h. The reaction solution is rotary evaporated and then added dropwisely into a cold diethyl ether, after the precipitate is filtrated and the product was vacuum freeze-dried to obtain the p-nitrophenylchloroformate-polyethylene glycol-tyramine copolymer (PNC-PEG-PNC):

(2) The p-nitrophenylchloroformate-polyethylene glycol-tyramine copolymer solution (PNC-PEG-PNC) obtained in step (1) is dissolved in a phosphate buffer, then a phosphate buffer of dissolved tyramine (TA) is added into the PNC-PEG-PNC solution, and reacted for 5~15 h at room temperature to obtain a p-nitrophenylchloroformate-polyethylene glycol-tyramine copolymer (PNC-PEG-tyramine) solution;

(3) ε-Polylysine is dissolved in a phosphate buffer. Then the p-nitrophenylchloroformate-polyethylene glycol-tyraminecopolymer (PNC-PEG-tyramine) solution obtained in step (2) is added into the ε-polylysine solution, and reacted for 12~72 h at room temperature, after completion of reaction p-nitrophenylchloroformate (PNC) salt precipitate is removed by filtration, the filtrate obtained after filtration is dialyzed in a purified water for 4 to 8 days, freeze-drying to obtain a ε-polylysine grafted with polyethylene glycol (PEG) and tyramine:

(4) The ε-polylysine grafted with polyethylene glycol (PEG) and tyramine obtained in step (3) is dissolved in water or a phosphate buffer. Then a mixed aqueous solution of horseradish peroxidase and hydrogen peroxide is added to the aboved solution, stirred at room temperature for 5~60 s to form a polylysine hydrogel.

In step (1), number average molecular weight of the polyethylene glycol is in the range of 4000 to 6000, preferably 4000.

In step (1), polyethylene glycol is dissolved in dichlormethane, such that the concentration of solute polyethylene glycol is 50 to 200 g/L, preferably 50 to 150 g/L: in the solution of p-nitrophenylchloroformate in dichlormethane, the concentration of the solute p-nitrophenylchloroformate is 20 to 40 g/L, preferably 25 to 35 g/L.

In step (1), at room temperature 4-dimethylaminopyridine and triethylamine are added and preferably reacted for 30 minutes.

In step (1), after addition is completed, reacted under room temperature and inert gas shielding condition preferably for 24 hours.

In step (1), the reaction mole ratio of polyethylene glycol, 4-dimethylaminopyridine, triethylamine, p-nitrophenylchloroformate is 1:2 to 5:2 to 5:2 to 5, preferably 1:3:3:3.

In step (1), the temperature of the cold diethyl ether is −4° C. to −20° C., preferably −4° C., the amount of the cold diethyl ether is 20 to 40 fold, preferably 30 fold of the reaction solution volume after the rotary evaporation.

In step (1), the temperature of the vacuum freeze-drying is −40° C. to −80° C., preferably at −60° C., and the pressure is 10 to 30 Pa, preferably 10 Pa.

In step (1), temperature of the rotary evaporation is 50° C., being rotary evaporated to 5 to 10%, preferably 5% of the original volume.

In step (1), all operations are conducted under room temperature and anhydrous and oxygen-free condition, the oxygen-free condition can be protected by introduction of an inert gas, preferably nitrogen gas.

In step (2), (3) and (4), the phosphate buffer is a phosphate buffer of pH 7.4, 0.01 to 0.2 mol/L, preferably a phosphate buffer of pH 7.4 and 0.01 Mol/L.

In step (2), p-nitrophenylchloroformate-polyethylene glycol-p-nitrophenylchloroformate copolymer is dissolved in a phosphate buffer, the concentration of solute p-nitrophenylchloroformate-polyethylene glycol-p-nitrophenylchloroformate copolymer is 50 to 100 g/L, preferably 80 g/L; in the phosphate buffer with dissolved tyramine, the concentration of the solute tyramine is 3 to 10 g/L, preferably 2 to 6 g/L.

In step (2), the mole ratio of p-nitrophenylchloroformate-polyethylene glycol-p-nitrophenylchloroformate copolymer to tyramine is 2:0.5 to 1.5, preferably 2:1.

In step (2), preferably reacted at room temperature for 10 hours to obtain p-nitrophenylchloroformate-polyethylene glycol-tyramine copolymer solution.

In step (2), all operations are conducted at room temperature and under oxygen-free condition, the oxygen-free condition can be protected by introduction of an inert gas, preferably nitrogen gas.

In step (3), polylysine is dissolved in a phosphate buffer, the concentration of solute polylysine is 0.43 to 1.09 g/L, preferably 0.4 to 0.8 g/L.

In step (3), the mole ratio of ε-polylysinetop-nitrophenylchloroformate-polyethylene glycol-p-nitrophenylchloroformate copolymer is 0.04 to 0.07:2, preferably 0.05:2.

In step (3), preferably reacted at room temperature for 24 hours.

In step (3), preferably dialyzed for 5 days.

In step (3), the temperature of the freeze-drying is −60° C.

In step (3), all operations are conducted at room temperature and under oxygen-free condition, the oxygen-free condition can be protected by introduction of an inert gas, preferably nitrogen gas.

In step (4), the ε-polylysine grafted with polyethylene glycol and tyramine obtained in step (3) is dissolved in water or a phosphate buffer, the concentration of the solute ε-polylysine grafted with polyethylene glycol and tyramine is 5 to 10 wt %, preferably 10 wt %.

In step (4), in the mixed water solution of horseradish peroxidase and hydrogen peroxide, the concentration of solute horseradish peroxidase and hydrogen peroxide in water solution are respectively 0.003 to 0.12 mg/mL and 0.02 to 0.07 wt %, preferably 0.12 mg/mL and 0.06 wt %.

In step (4), all reaction operations are conducted under a room temperature and oxygen-free condition, the oxygen-free condition can be protected by introduction of an inert gas, preferably nitrogen gas.

The ε-polylysine hydrogel obtained by the above-described method is also within the protection scope of the present invention.

Application of the above-described ε-polylysine hydrogel in preparation as wound dressing, it can be used in medical or cosmetic fields.

Beneficial effect: The present invention prepares a hydrogel medical material of polylysine-polyethylene glycol-tyramine three-dimensional network structure by using natural polymeric material polylysine as wound dressing scaffold, and modifying the polylysine molecular scaffold by grafting with polyethylene glycol and tyramine, then treated by horseradish peroxidase and hydrogen peroxide; this wound dressing material has many advantages such as high mechanical strength, short gelation time and adjustable gel strength, mild reaction condition, and low tissue toxicity, and overcomes many shortcomings such as low material mechanical strength, poor biocompatibility, high cytotoxicity of the existing wound dressing, having an extensive application prospect in medical field.

DESCRIPTION OF THE EMBODIMENTS

Based on the following examples, the present invention can be better understood. However, a person skilled in the art will readily understood that, the contents described in the examples are only used to illustrate the present invention, and should not and will not restrain the present invention described in detail in the claims.

The resources of reagents used in the following examples are as follows:

ε-polylysine: purchased from Nanjing Shineking Biological Technology Co., Ltd.:

PNC (p-nitrophenylchloroformate), DMAP (4-dimethylaminopyridine): purchased from Sigma-Aldrich Company; TA (tyramine) purchased from Energy chemical;

TEA (triethylamine), PEG (polyethylene glycol) purchased from Sinopharm Chemical Reagent Co., Ltd.

The resources of equipments used in the following examples are as follows:

Magnetic stirrer: Type 85-2C, Shanghai Niuhang Instrument and Equipment Co., Ltd.

Freeze-dryer: Type FD-1C-50, Beijing Boyikang Experimental Instrument Co., Ltd.

Vacuum drying box: Type YZG-600, Nanjing Yantai Electrical Heating Equipment Co., Ltd.

Infrared spectrometer: Type Nicolet 380, Thermo Company, USA.

NMR spectrometer: Type AVANCE AV-500, Bruker Daltonics Company, USA.

Example 1: Preparation of PNC-PEG-PNC 20 g (5 mmol) of PEG4000 was weighed and placed into a 500 ml three-neck flask under room temperature and anhydrous and oxygen-free condition, and 400 ml anhydrous dichlormethane was added to the flask, after PEG was completely dissolved under magnetic stirring. Then 1.832 g (15 mmol) of DMAP and 1.518 g (15 mmol) of TEA were added, stirred and reacted for 30 min under room temperature and nitrogen gas shielding. The reaction was added dropwisely into 3.022 g (15 mmol) PNC solution (using 100 ml anhydrous dichlormethane as the solvent), after addition is completed at room temperature the reaction solution was concentrated to 25 ml with a rotary evaporator, then added dropwisely into a cold diethyl ether of −4° C., the amount of the cold diethyl ether was 750 ml, after the formed precipitate was removed by filtration, and freeze-dried at −60° C. at 10 Pa vacuum to obtain a PNC-PEG-PNC copolymer, the yield was 79%.

Example 2: Preparation of PNC-PEG-PNC

PEG4000 20 g (5 mmol) was weighed and placed into a 500 ml three-neck flask under room temperature and anhydrous and oxygen-free condition, and 200 ml anhydrous dichlormethane was added to the flask. Then PEG was completely dissolved under magnetic stirring. 1.832 g (15 mmol) of DMAP and 1.518 g (15 mmol) of TEA were added, stirred and reacted at room temperature for 30 min, after completion of reaction it was added dropwisely to 3.022 g (15 mmol) of PNC solution (using 100 ml anhydrous dichlormethane as the solvent), after addition is complete stirred and reacted for 24 hours under room temperature and nitrogen gas shielding, after completion of reaction. The reaction solution was concentrated to 15 ml with a rotary evaporator, then added dropwisely into a cold diethyl ether of −4° C., the amount of the cold diethyl ether was 450 ml, the formed precipitate was removed by filtration, then vacuum freeze-dried under −60° C. at 10 Pa to obtain a PNC-PEG-PNC copolymer, the yield was 87%.

Example 3: Preparation of PNC-PEG-PNC

PEG6000 20 g (5 mmol) was weighed and placed into a 500 ml threer-neck flask under room temperature and anhydrous and oxygen-free condition, and 100 ml of anhydrous dichlormethane was added to the flask. Then the PEG was completely dissolved under magnetic stirring 1.832 g (15 mmol) of DMAP and 1.518 g (15 mmol) of TEA were added, stirred and reacted at room temperature for 30 minutes, after completion of reaction it was added dropwisely into a 3.022 g (15 mmol) of PNC solution (using 100 ml anhydrous dichlormethane as the solvent), after addition is completed stirred and reacted for 24 hours at room temperature and under nitrogen gas shielding, after completion of reaction. The reaction solution was concentrated to 10 ml with a rotary evaporator, then added dropwisely into a cold diethyl ether of −4° C., the amount of the cold diethyl ether was 300 ml, the formed precipitate was removed by filtration then freeze-dried under −60° C. at 10 Pa vacuum to obtain a PNC-PEG-PNC copolymer, the yield was 62%.

Example 4: Preparation of PNC-PEG-PNC 20 g of PEG4000 (5 mmol) was weighed and placed in a 500 ml three-neck flask under room temperature and anhydrous oxygen-free condition, and 200 ml of anhydrous dichlormethane was added to the flask. Then PEG was completely dissolved under magnetic stirring 1.832 g (15 mmol) of DMAP and 1.518 g (15 mmol) of TEA were added, stirred and reacted at room temperature for 30 minutes, after completion of reaction it was added dropwisely into a 3.022 g (15 mmol) of PNC solution (using 120 ml anhydrous dichlormethane as the solvent), after addition is complete stirred and reacted for 24 hours under room temperature and under nitrogen gas shielding, after completion of the reaction. The reaction solution was concentrated to 16 ml with a rotary evaporator, then added dropwisely into a cold diethyl ether of −4° C., the amount of the cold diethyl ether was 480 ml, the formed precipitate was removed by filtration then vacuum freeze-dried under −60° C. at 10 Pa to obtain PNC-PEG-PNC copolymer, the yield was 77%.

Example 5: Preparation of PNC-PEG-PNC 20 g (5 mmol) of PEG4000 was weighed and placed in a 500 ml three-neck flask under room temperature and anhydrous and oxygen-free condition, and 200 ml of anhydrous dichlormethane was added to the flask. Then PEG was completely dissolved under magnetic stirring 1.832 g (15 mmol) of DMAP and 1.518 g (15 mmol) of TEA were added, stirred and reacted at room temperature for 30 minutes, after completion of reaction it was added dropwisely into a 3.022 g (15 mmol) PNC solution (using 86 ml anhydrous dichlormethane as the solvent), after addition is complete stirred and reacted for 24 hours under room temperature and under nitrogen gas shielding, after completion of reaction. The reaction solution was concentrated to 14.3 ml with a rotary evaporator then added dropwisely into a cold diethyl ether of −4° C., the amount of the cold diethyl ether was 429 ml, the formed precipitate was removed out by filtration then vacuum freeze-dried under −60° C. at 10 Pa to obtain PNC-PEG-PNC copolymer, the yield was 53%.

Example 6: Preparation of PNC-PEG-PNC

The method is the same as Example 1, the difference is controlling the feeding mole ratio of PEG, DMAP, TEA, PNC to 1:2:2:3, the yield of PNC-PEG-PNC obtained was 43%.

Example 7: Preparation of PNC-PEG-PNC

The method is the same as Example 1, the difference is controlling the feeding mole ratio of PEG, DMAP, TEA, PNC to 1:2:5:3, the yield of PNC-PEG-PNC obtained was 51%.

Example 8: Preparation of PNC-PEG-PNC

The method is the same as Example 1, the difference is controlling the feeding mole ratio of PEG, DMAP, TEA, PNC to 1:5:2:3, the yield of PNC-PEG-PNC obtained was 38%.

Example 9: Preparation of PNC-PEG-PNC

The method is the same as Example 1, the difference is controlling the feeding mole ratio of PEG, DMAP, TEA, PNC to 1:5:5:3, the yield of the PNC-PEG-PNC obtained was 69%.

Example 10: Preparation of PNC-PEG-PNC

The method is the same as Example 2, the difference is after addition of DMAP and TEA, stirred and reacted at room temperature for 20 minutes, the yield of PNC-PEG-PNC obtained was 64%.

Example 11: Preparation of PNC-PEG-PNC

The method is the same as Example 2, the difference is after addition of DMAP and TEA, stirred and reacted at room temperature for 150 minutes, the yield of the PNC-PEG-PNC obtained was 81%.

Example 12: Preparation of $\epsilon$-polylysine Grafted with PEG and Tyramine

Under room temperature and oxygen-free condition, 0.069 g (0.5 mmol) of TA was weighed and dissolve in a 14 ml phosphate buffer of pH 7.4 and 0.01M, meanwhile 4 g (2 mmol) of PNC-PEG-PNC copolymer obtained in Example 2 was dissolved in a 50 ml phosphate buffer of pH 7.4 and 0.01M, after PNC-PEG-PNC was completely dissolved, tyramine phosphate solution was added under oxygen-free condition, stirred and reacted at room temperatures for 10 h, after the reaction is completed a PNC-PEG-tyramine copolymer solution was obtained; under room temperature and oxygen-free condition, 0.14 g (0.04 mmol) of $\epsilon$-polylysine was weighed and dissolved in 280 ml phosphate buffer of pH 7.4, 0.01M, after $\epsilon$-polylysine was completely dissolved and added into the PNC-PEG-tyramine copolymer solution, stirred and reacted at room temperature for 24 h, after completion of reaction the PNC salt was removed by filtration, the mixed solution was placed in a dialysis bag with a molecular weight cutoff being 7000 Da, then the unreacted materials and byproducts were dialyzed and removed in a large amount of ultra-pure water, the ultra-pure water was replaced 5-6 times every day, and dialyzed for 5 days, finally freeze-dried at −60° C. to obtain a $\epsilon$-polylysine grafted with PEG and tyramine, the yield was 65%.

Example 13: Preparation of $\epsilon$-polylysine Grafted with PEG and Tyramine

Figure 1:
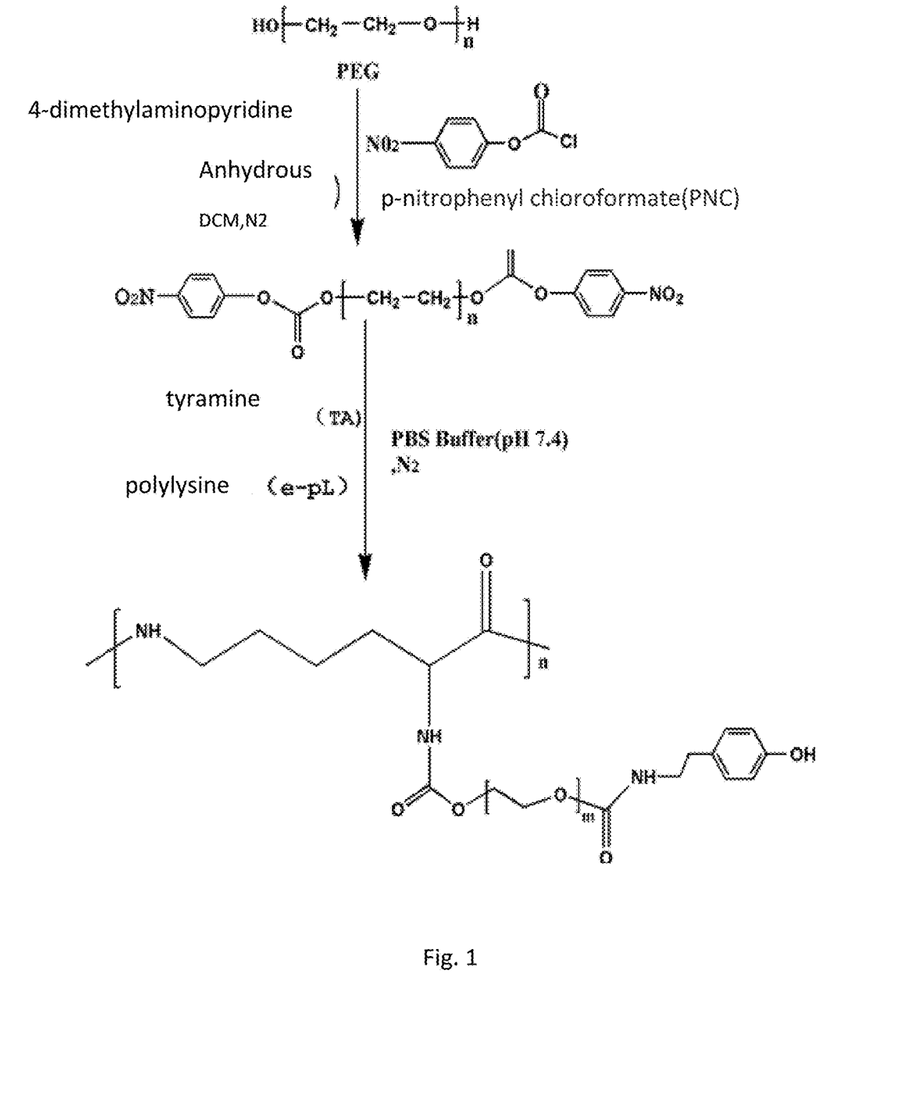
FIG. 1 is a schematic diagram and molecular structure of polylysine-polyethylene glycol-tyramine.
Figure 2:
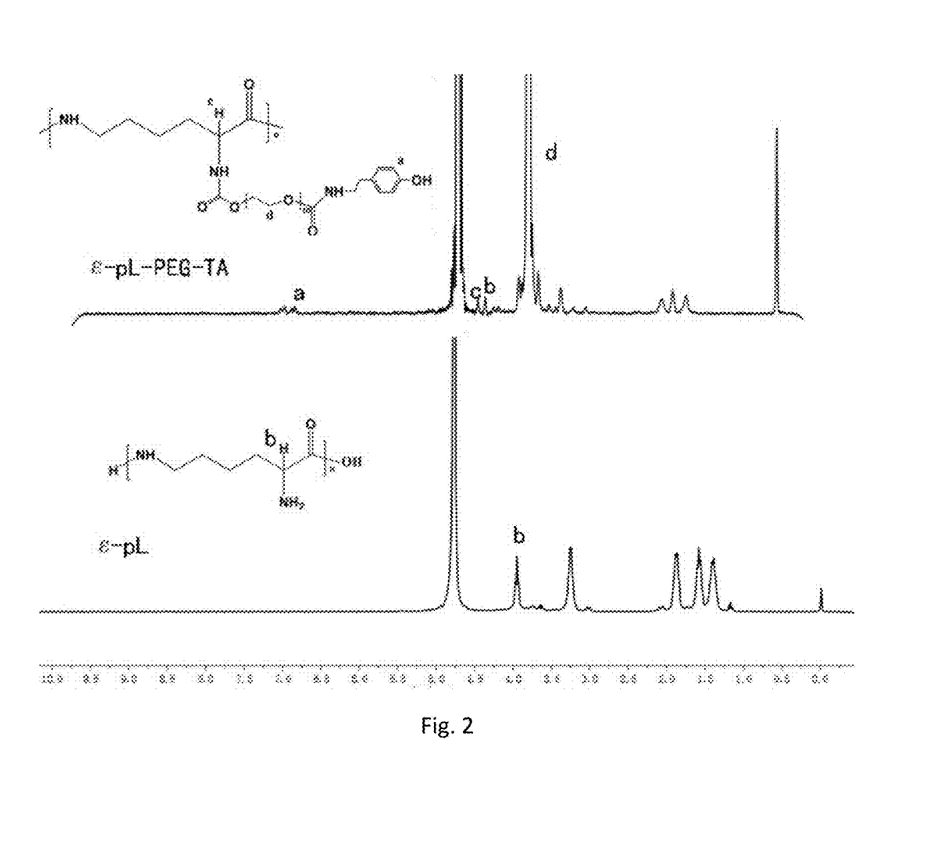
FIG. 2 is the $^1$H-NMR spectrum of polylysine, polylysine-polyethylene glycol-tyramine, the solvent is $D_2O$.

Under room temperature and oxygen-free condition, 0.137 g (1 mmol) of TA was weighed and dissolved in 28 ml phosphate buffer of pH 7.4 and 0.01M, meanwhile 4 g (2 mmol) of PNC-PEG-PNC copolymer obtained in Example 2 was dissolved in a 50 ml phosphate buffer of pH 7.4 and 0.01M, after PNC-PEG-PNC was completely dissolved, a tyramine phosphate solution was added into under oxygen-free condition, stirred and reacted at room temperature for 10 h, after completion of the reaction a PNC-PEG-tyramine copolymer solution was obtained; under room temperature and oxygen-free condition, 0.14 g (0.04 mmol) of $\epsilon$-polylysine was weighed and dissolved in 280 ml phosphate buffer of pH 7.4 and 0.01M, after $\epsilon$-polylysine was completely dissolved, then it was added to a PNC-PEG-tyramine copolymer solution, stirred and reacted for 24 h at room temperature, after completion of reaction PNC salt was removed by filtration, the mixed solution was placed in a dialysis bag with a molecular weight cutoff being 7000 Da, then the unreacted materials and byproducts were dialyzed and removed in a large amount of ultra pure water, the ultra pure water was replaced 5-6 times every days, dialyzed for 5 days, finally freeze-dried at −60° C. to obtain a ε-polylysine grafted with PEG and tyramine, the yield was 77%. From FIG. 2, the lower diagram is H-NMR spectrum of the polylysine, and the upper diagram is H-NMR spectrum of the synthesized ε-pL-PEG-TA; it can be seen that, on basis of original base peak of the polylysine, the peaks of chemical shift being 3.5 and 7.0 corresponding to characteristic peak of grafted PEG and tyramine, respectively, indicating the ε-pL-PEG-TA is correctly synthesized.

Example 14: Preparation of ε-polylysine Grafted with PEG and Tyramine

The method is the same as Example 12, the difference is controlling the feeding mole ratio of PNC-PEG-PNC, TA, ε-polylysine (ε-pL) to 2:1.5:0.04, the yield of the ε-pL-PEG-TA obtained was 69%.

Example 15: Preparation of a ε-polylysine Grafted with PEG and Tyramine

The method is same as Example 12, the difference is controlling the feeding mole ratio PNC-PEG-PNC, TA, ε-polylysine (ε-pL) to 2:1:0.06, the yield of ε-pL-PEG-TA obtained was 58%.

Example 16: Preparation of ε-polylysine Grafted with PEG and Tyramine

The method is the same as Example 12, the difference is controlling the feeding mole ratio of PNC-PEG-PNC, TA, ε-polylysine (ε-pL) to 2:1.5:0.07, the yield of the ε-pL-PEG-TA obtained was 63%.

Example 17: Preparation of ε-polylysine Grafted with PEG and Tyramine

The method is the same as Example 12, the difference is, after the PNC-PEG-PNC was completely dissolved, a tyramine phosphate solution was added under oxygen-free condition, and stirred and reacted at room temperature for 5 h, the yield of the ε-pL-PEG-TA obtained was 45%.

Example 18: Preparation of a ε-polylysine Grafted with PEG and Tyramine

The method is the same as Example 12, the difference is, after PNC-PEG-PNC was completely dissolved, a tyramine phosphate solution was added under oxygen-free condition, wherein stirred and reacted for 15 h at room temperature, the yield of ε-pL-PEG-TA obtained was 72%.

Example 19: Preparation of a ε-polylysine Grafted with PEG and Tyramine

The method is the same as Example 12, the difference is, after ε-polylysine was completely dissolved, it was added into the PNC-PEG-tyramine copolymer solution, and stirred and reacted at room temperature for 12 h, the yield of the ε-pL-PEG-TA obtained was 29%.

Example 20: Preparation of ε-polylysine Grafted with PEG and Tyramine

The method is the same as Example 12, the difference is, after ε-polylysine was completely dissolved, it was added into the PNC-PEG-tyramine copolymer solution, stirred and reacted at room temperature for 72 h, the yield of the ε-pL-PEG-TA obtained was 67%.

Example 21: Preparation of Hydrogel

The ε-polylysine copolymer grafted with PEG and tyramine obtained in Example 13 was dissolved in a phosphate buffer of pH 7.4 and 0.01 M, to prepare a solution with concentration being 10 wt %, then horseradish peroxidase (enzyme activity>250U, Sigma) and hydrogen peroxide were added, the final concentrations of horseradish peroxidase and hydrogen peroxide were respectively 0.03 mg/ml, 0.06 wt %, and magnetic stirring was conducted at 25° C. to form a polylysine hydrogel, its gelation time was 30 s.

Example 22: Preparation of Hydrogel

The ε-polylysine copolymer grafted with PEG and tyramine obtained in Example 13 was dissolved in a phosphate buffer of pH 7.4 and 0.01 M, to prepare a solution with a concentration being 10 wt %, then horseradish peroxidase (enzyme activity>250 U, Sigma) and hydrogen peroxide were added, the final concentrations of horseradish peroxidase and hydrogen peroxide were respectively 0.05 mg/ml, 0.06 wt %, and magnetic stirring was conducted at 25° C. to form a polylysine hydrogel, its gelation time was 25 s.

Example 23: Preparation of Hydrogel

The ε-polylysine copolymer grafted with PEG and tyramine obtained in Example 13 was dissolved in a phosphate buffer of pH 7.4 and 0.01 M, to prepare a solution with a concentration being 10 wt %, and horseradish peroxidase (enzyme activity>250 U, Sigma) and hydrogen peroxide were added, the final concentrations of horseradish peroxidase and hydrogen peroxide were respectively 0.08 mg/ml, 0.06 wt %, and magnetic stirring was conducted at 25° C. to form a polylysine hydrogel, its gelation time was 22 s.

Example 24: Preparation of Hydrogel

The ε-polylysine copolymer grafted with PEG and tyramine obtained in Example 13 was dissolved in a phosphate buffer of pH 7.4 and 0.01 M, to prepare a solution of a concentration being 10 wt %, and horseradish peroxidase (enzyme activity>250U, Sigma) and hydrogen peroxide were added, the final concentrations of horseradish peroxidase and hydrogen peroxide were respectively 0.12 mg/L, 0.06 wt %, and magnetic stirring was conducted at 25° C. to form a polylysine hydrogel, its gelation time was 5 s.

Example 25: Preparation of Hydrogel

The method is the same as Example 21, the difference is controlling the concentration of the hydrogen peroxide to 0.04 wt %, and magnetic stirring was conducted at 25° C. to form a polylysine hydrogel, its gelation time was 17 s.

Example 26: Preparation of Hydrogel

The method is the same as Example 21, the difference is controlling the concentration of the hydrogen peroxide to 0.02 wt %, and magnetic stirring was conducted at 25° C. to form a polylysine hydrogel, its gelation time was 39 s.

Example 27: Preparation of Hydrogel

The method is the same as Example 21, the difference is controlling the concentration of the hydrogel material ε-pL-PEG-TA to 7 wt %, and magnetic stirring was conducted at 25° C. to form a polylysine hydrogel, its gelation time was 25 s.

Example 28: Preparation of Hydrogel

The method is the same as Example 21, the difference is controlling the concentration of hydrogel material ε-pL-PEG-TA to 5 wt %, and magnetic stirring was conducted at 25° C. to form a polylysine hydrogel, its gelation time was 54 s.

Example 29

Figure 3:
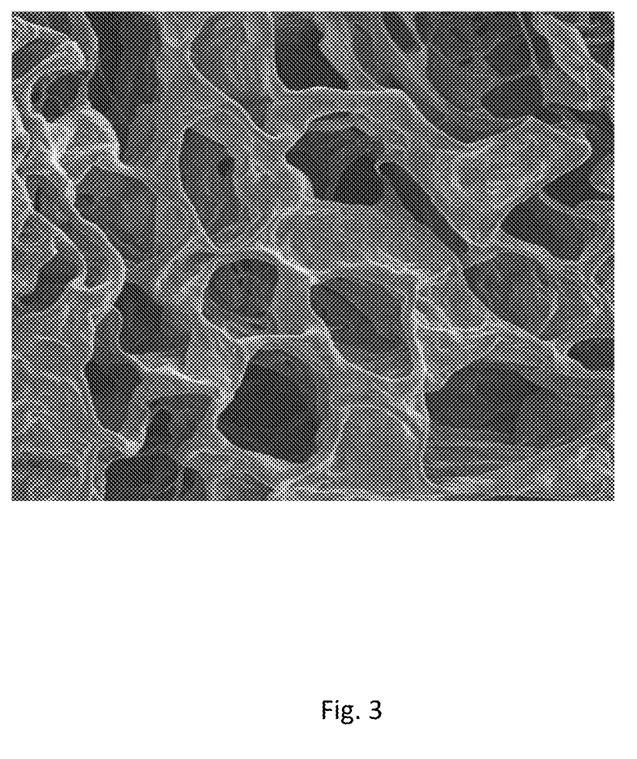
FIG. 3 is an electron microscope image (SEM) of polylysine-polyethylene glycol-tyraminehydrogel.

After the polylysine-PEG-tyramine hydrogel sample prepared in Example 24 was freeze-dried, a small amount of the sample was fixed on a silicon wafer, then air dried overnight, its surface crosslinking morphology was observed under a CEM (×100), as shown in FIG. 3.

Example 30: Wound Healing Experiment

Figure 4:
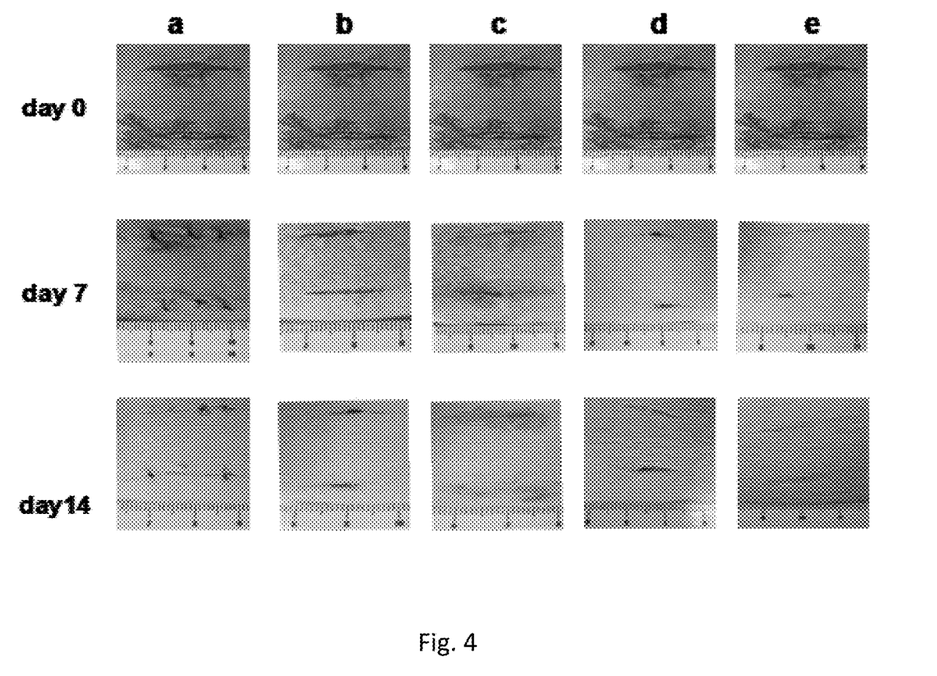
FIG. 4 is a rat back wound healing experiment, a) artificial suture, b) fibrin glue dressing treated group, c) cyanoacrylate dressing treates group, d) polylysine-polyethylene glycol hydrogel dressing, e) polylysine hydrogel dressing of the present invention.

After the back of rats were sheared, and unhaired with a sodium sulfide solution for 48 h, each rat was subcutaneously injected 0.5 mL of 0.5% lidocaine injection for local anesthesia, totally at 3 sites, two circular skin incisions of about 2.0 cm diameter were sheared at back with surgical scissors, disinfected with a 70 v/v % ethanol, the wound dressing in Example 1 was coated at the wound, Control Group I was sutured with a conventional surgical needle and thread, Control Group II was coated with a commercially available medical wound dressing fibrin glue, Control Group III was coated with a commercially available medical wound dressing Dermabond, Control Group IV was coated with polylysine-PEG hydrogel [*Polylysine-Modified PEG-Based Hydrogels to Enhance the Neuro-Electrode Interface*, Journal of Biomaterials Science, Polymer Edition Volume 22, Issue 4-6, 2011]. During the experiment, each group had no bacteria infection, the wound healing were observed respectively after 0, 7, 14 days. See FIG. 5, a) is a control group of artificial suture healing, b) is fibrin glued dressing treated group, c) is cyanoacrylate dressing treated group, d) is polylysine-PEG (polyethylene glycol) hydrogel dressing treated group, e) is a group treated by the polylysine hydrogel dressing of the present invention. With extension of treatment time, the rats in four groups were all healed, the hydrogel dressing treated groups were all superior to the group treated only with the suture; in the group treated by using ε-polylysine cross-linked polymer hydrogel dressing, the wound area was obviously decreased, and the healing was rapid, and the surface was smooth and flat, showing a good biocompatibility and ability of promoting wound healing.

Comprehensive evaluation: the ε-polylysine hydrogel wound dressing of the present invention has a good biocompatibility, and contributes to cell adhesion and growth, it has a promotion effect to wound healing, and can effectively reduce leakage of tissue fluid, having an extensive application prospect in the medical wound dressing field.

What is claimed is:

1. A ε-polylysine hydrogel has the following constitutional unit:

wherein, n is any natural number of 20 to 30, m is any natural number of 50 to 70.

2. A process for preparing the ε-polylysine hydrogel of claim 1, comprises the following steps:
   (1) adding a polyethylene glycol into dichlormethane, adding 4-dimethylaminopyridine and triethylamine reacting for 20~150 min at room temperature; then adding dropwisely the reaction mixture into a solution of p-nitrophenylchloroformate in dichlormethane under inert gas shielding condition at room temperature, reacting for 12 to 72 hours; evaporating and then adding dropwisely into a cold diethyl ether solution; removing precipitates from mixed solution by filtration and vacuum freeze-drying to obtain a p-nitrophenylchloroformate-polyethylene glycol-p-nitrophenylchloroformate copolymer;
   (2) dissolving the p-nitrophenylchloroformate-polyethylene glycol-p-nitrophenylchloroformate copolymer into a phosphate buffer; then adding a tyramine dissolved in the phosphate buffer, reacting for 5 to 72 hours at room temperature to obtain a solution of p-nitrophenylchloroformate-polyethylene glycol-tyramine copolymer;
   (3) dissolving a ε-polylysine into the phosphate buffer, then adding the p-nitrophenylchloroformate-polyethylene glycol-tyramine copolymer solution from step (2), and reacting at room temperature for 12 to 72 hours; removing the p-nitrophenylchloroformate precipitate by filtration, following by dialyzing the filtrate in purified water for 4 to 8 days; freeze-drying the filtrate to obtain a ε-polylysine grafted with polyethylene glycol and tyramine;
   (4) dissolving the ε-polylysine-polyethylene glycol-tyramine from step (3) into the water or phosphate buffer; adding a mixed aqueous solution of horseradish peroxidase and hydrogen peroxide; and stirring for 5 to 60 seconds at room temperature to form the ε-polylysine hydrogel.

3. The process according to claim 2, characterized in that, in step (1), dissolving polyethylene glycol in dichlormethane, such that the concentration of the solute polyethylene glycol is 50 to 200 g/L; in the solution of p-nitrophenylchloroformate in dichlormethane, the concentration of the solute p-nitrophenylchloroformate is 20 to 40 g/L.

4. The process according to claim 2, characterized in that, in step (1), the reaction mole ratio of polyethylene glycol, 4-dimethylaminopyridine, triethylamine, p-nitrophenylchloroformate is 1:2 to 5:2 to 5:2 to 5.

5. The process according to claim 2, characterized in that, in step (1), the temperature of the cold diethyl ether is −4° C. to −20° C., the amount of the cold diethyl ether is 20 to 40 fold of volume of the reaction solution after the evaporation.

6. The process according to claim 2, characterized in that, in step (1), the temperature of the vacuum freeze-drying is −40° C. to −80° C., and the pressure is 10 to 30 Pa.

7. The process according to claim 2, characterized in that, in step (1), all reactions are conducted under the room temperature and anhydrous and oxygen-free condition.

8. The process according to claim 2, characterized in that, in step (2), (3) and (4), the phosphate buffer being a phosphate buffer of pH 7.4 and 0.01 to 0.2 mol/L.

9. The process according to claim 2, characterized in that, in step (2), dissolving p-nitrophenylchloroformate-polyethylene glycol-p-nitrophenylchloroformate copolymer in the phosphate buffer, the concentration of the solute nitrophenyl chloroformate-polyethylene glycol-p-nitrophenylchloroformate copolymer is 50 to 100 g/L; in the tyramine phosphate buffer, the concentration of the tyramine is 3 to 10 g/L.

10. The process according to claim 2, characterized in that, in step (2), the mole ratio of p-nitrophenylchloroformate-polyethylene glycol-p-nitrophenylchloroformate copolymer to tyramine is 2:0.5 to 1.5.

11. The process according to claim 2, characterized in that, in step (2), all reactions are conducted under the room temperature and oxygen-free condition.

12. The process according to claim 2, characterized in that, in step (3), dissolving polylysine in the phosphate buffer, and the concentration of the polylysine is 0.43 to 1.09 g/L.

13. The process according to claim 2, characterized in that, in step (3), the mole ratio of $\epsilon$-polylysine to p-nitrophenylchloroformate-polyethylene glycol-p-nitrophenylchloroformate copolymer is 0.04 to 0.07:2.

14. The process according to claim 2, characterized in that, in step (3), all reactions are conducted under the room temperature and oxygen-free condition.

15. The process according to claim 2, characterized in that, in step (4), dissolving the $\epsilon$-polylysine grafted with PEG (polyethylene glycol) and tyramine obtained in step (3) in water or phosphate buffer, the concentration of the $\epsilon$-polylysine grafted with PEG (polyethylene glycol) and tyramine is 10 to 15% of weight.

16. The process according to claim 2, characterized in that, in step (4), in the mixed aqueous solution of horseradish peroxidase and hydrogen peroxide, the concentration of the solute horseradish peroxidase and hydrogen peroxide in aqueous solution is 0.003 to 0.12 mg/mL and 0.02 to 0.07% of weight, respectively.

17. The process according to claim 2, characterized in that, in step (4), all reactions are conducted under the room temperature and oxygen-free condition.

18. A process for treating a wound comprising a step of administering the $\epsilon$-polylysine hydrogel of claim 1 to a patient in need of would treatment.

* * * * *